(12) United States Patent
Hastwell

(10) Patent No.: US 8,551,403 B2
(45) Date of Patent: Oct. 8, 2013

(54) DISC SUBSTRATES FOR COMBINATORIAL CHEMISTRY

(75) Inventor: Peter Hastwell, North Adelaide (AU)

(73) Assignee: Raustech PTY Ltd., North Adelaide, South Australia (AU)

( * ) Notice: Subject to any disclaimer, the term of this patent is extended or adjusted under 35 U.S.C. 154(b) by 818 days.

(21) Appl. No.: 11/908,178

(22) PCT Filed: Mar. 10, 2006

(86) PCT No.: PCT/AU2006/000313
§ 371 (c)(1),
(2), (4) Date: Oct. 26, 2007

(87) PCT Pub. No.: WO2006/094356
PCT Pub. Date: Sep. 14, 2006

(65) Prior Publication Data
US 2008/0194425 A1      Aug. 14, 2008

(30) Foreign Application Priority Data

Mar. 10, 2005    (AU) ................................ 2005901147

(51) Int. Cl.
*G01N 35/02*       (2006.01)
(52) U.S. Cl.
USPC ........... 422/64; 422/82.05; 422/65; 369/53.2; 369/53.31; 506/33; 506/39; 435/6.12
(58) Field of Classification Search
USPC ........... 422/57, 64, 82.05; 435/6, 288.5, 91.1, 435/91.2
See application file for complete search history.

(56) References Cited

U.S. PATENT DOCUMENTS

| | | | |
|---|---|---|---|
| 5,751,629 A * | 5/1998 | Nova et al. | 506/33 |
| 6,342,349 B1 * | 1/2002 | Virtanen | 506/39 |
| 6,395,562 B1 | 5/2002 | Hammock et al. | |
| 7,200,088 B2 * | 4/2007 | Worthington et al. | 369/53.31 |
| 7,267,938 B2 * | 9/2007 | Anderson et al. | 435/4 |
| 7,718,129 B2 | 5/2010 | Mamine et al. | |

FOREIGN PATENT DOCUMENTS

| | | |
|---|---|---|
| JP | H11-511238 A | 9/1999 |
| JP | 2002014106 A | 1/2002 |
| JP | 2002-52166 A | 7/2002 |
| JP | 2005-003450 A | 1/2005 |
| WO | 96/36436 A1 | 11/1996 |
| WO | 9812559 A1 | 3/1998 |
| WO | 0246761 A2 | 6/2002 |
| WO | 03087827 A2 | 10/2003 |
| WO | 2005001121 A1 | 1/2005 |

OTHER PUBLICATIONS

Japanese Office Action for corresponding Japanese Application No. 2008-500008 with translation of reasoning.

* cited by examiner

*Primary Examiner* — Sally Merkling
(74) *Attorney, Agent, or Firm* — Rothwell, Figg, Ernst & Manbeck P.C.

(57) ABSTRACT

A combinatorial chemical formation and assay disc (1) having a base (20) and an upper surface (26) and a lower surface, one of the upper or lower surfaces being an assay surface and a data surface (40) spaced from the assay surface wherein the data surface is on or within the assay disc. The assay surface has a conductive layer (64) on the base, a dielectric or photoconductive layer (66) on the conductive layer and a chemically functional layer (68, 69) on the dielectric or photoconductive layer. The assay surface may be planar or include three dimensional features (100, 168).

20 Claims, 8 Drawing Sheets

DISC SUBSTRATES FOR COMBINATORIAL CHEMISTRY

This application is a 371 filing of PCT/AU2006/000313, filed Mar. 10, 2006, which claims priority from Australian patent application number 2005901147, filed Mar. 10, 2005. These applications are incorporated herein by reference.

FIELD OF INVENTION

This invention relates to a disc system for creating and providing substrates for combinatorial chemical formation and assay and in one particular embodiment relates to a biochemical assay disc.

BACKGROUND

There have been a number of proposals for preparation of combinatorial chemistry "chips" for performing assays such as DNA assays. In the case of DNA chips these have a number of defined features, DNA oligomers for instance, on their surface which are formed, by a number of different processes. When a sample including DNA fragments is passed over the surface of the chip, where DNA hybridisation occurs, which can be located by use of a suitable fluorescing compound on the DNA fragments, the type of DNA may be ascertained. These techniques may be used to determine the types of DNA that may be present in the DNA sample.

There can be problems, however, with addressing all the features on an assay chip and also problems synthesising the features, such as the DNA oligomers, on the various assay chip and it is to providing a substrate upon which features, such as DNA oligomers, can be synthesised that the present invention is directed.

In its broadest form the invention relates to the spatially defined deposition of any of a wide variety of chemical substances onto a disc surface and to discs having such surfaces. Substances may include, but are not limited to, coloured materials, dyes, drug molecules, polymers, catalysts, antiwetting agents, pigments, etching chemicals, layerings and reagents for de-blocking, blocking, derivatisation and activation of solid phase chemical groups. Arrays can include deoxyribonucleic acids (DNA), peptides, peptidenucleic acids (PNA), ribonucleic acids (RNA) and other solid phase chemical arrays and arrays assembled by combinatorial chemistry.

The invention will be generally discussed in relation to its application to biochemical assay of biological samples such as DNA fragments but the invention is not so limited but can extend to other forms of combinatorial chemistry that can be carried out on a assay disc. This biochemical application invention will be mainly discussed in relation to DNA but the invention is not so limited but can extend to other peptides, peptidenucleic acids (PNA), ribonucleic acids (RNA) and other solid phase biochemical arrays.

Optical disc technology is well understood and suitable technology is available for writing and reading optical discs. An optical disc essentially consists of a substantially planar disc with a data surface moulded into a transparent material within the disc and which can be read using a suitable laser technique which tracks a spiral of pits on the data surface. The term data surface is used in this specification to describe such a spiral of data bits on a suitable disc format.

The optical disc format may be a compact disc (CD), a digital video disc (DVD) or nanometer (blue light readable) disc (Blu Ray™). The difference relates to the number of data bits which can be placed on a disc and the spacing and size of those data bits. Reading can be achieved by use of a laser of a selected wavelength which can give different data densities. The shorter wavelengths allow higher pit densities for reading and writing.

DESCRIPTION OF THE INVENTION

In one form, therefore, although this may not necessarily be the only or broadest form the invention is said to reside in a combinatorial chemical formation and assay disc having a base and an upper surface and a lower surface one of the upper or lower surfaces being an assay surface and a data surface spaced from the assay surface wherein the data surface is on or within the assay disc.

The assay surface and the data surface may be spaced radially apart on the disc. Hence the data surface may be placed on an inner annular region of the disc and the assay surface may be on an outer annular region of the disc or vice versa. Alternatively the assay surface may be above the data surface in the same annular region of the disc.

In one embodiment of the invention the assay surface may comprise a plurality of zones each of which can function as an independent assay surface so that the disc can be used for a plurality of assays. These zones may be defined by separate segments of the disc or by multiple starts in spiral zones on the assay surface of the disc. In use, the multiple zones may be written and read concurrently so that better accuracy and a degree of redundancy is provided for. The assays may for instance be bio-assays.

In one embodiment of the invention the assay surface can comprise an array of linker molecules or be a surface to receive linker molecules thereon and thereby being adapted for direct photo-conductor activated combinatorial chemistry thereon.

In one embodiment of the invention the assay surface comprises a conductive layer on the base; a dielectric layer of a material which will hold an electrostatic charge; and a chemically functional layer, the chemically functional layer providing a protective layer for the dielectric layer and a chemically reactive surface for covalent attachment and synthesis of compounds or deposition of compounds on the surface; whereby electrostatic charge patterns may be formed in a predetermined manner upon or in the substrate.

In one embodiment the conductive layer may be in the form of a conductive material which presents a mirror surface and the photoconductive layer may be transparent or translucent. In such a situation the mirror surface can in effect provide an increase in light by reflection with a subsequent gain in exposure light efficiency and reading laser light.

The conductive layer or an electrical connection from the conductive layer preferably extends to a central portion or other region of the disc such that when it is clamped into a processing device as discussed below the conductive layer is earthed or becomes part of an electrical circuit.

In one embodiment the base may be transparent whereby the data on the data surface can be read through the assay surface and the base. This can be achieved because the laser which is used to read the data surface through the assay layer and the base is relatively unfocused at the assay surface and therefore components on the assay surface will not interfere with the reading of the data surface.

In an alternative embodiment the assay surface may be written or formed and read from one side of the disc and the data surface is adapted to be read from the other side of the disc through the base.

Preferably the data surface includes at least a program portion which contains information about how an assay is to be carried out and/or the location of the various features on the assay surface as well as the data surface having address locations so that the various assay features on an assay disc can be located and addressed. Alternatively the data surface or information on address locations may be interleaved with the assay features on the assay surface.

There can be further included a lid or cover portion which can be fitted onto the disc on the assay surface side so that the assay surface is thereby protected. The assay surface may for instance be protected from dust. This cover can be removed so that the assay surface can be written and read or may include ports for providing chemicals to the assay surface during formation processes on the surface and analytes and the like to the assay surface during analysis.

Alternatively the disc may be supplied in a sealed cassette and equipment to write and read the disc can include a mechanism to automatically open the sealed cassette within a dust free environment of a writing, hybridisation or reading device.

In one embodiment the disc comprises a substantially planar disc, a central aperture to receive a spindle and clamping mechanism to enable the disc to be rotated. The disc may comprise a plurality of annular areas including a clamp area adjacent to the aperture, a run in area, a program area, and assay area and a run out area. There may further be inner and outer circumferential sealing areas.

In a preferred form of the invention the assay surface comprises three dimensional features, the assay surface being at a selected level on the three dimensional features whereby to increase the light contrast between assay areas and non-assay areas on other levels on the assay surface. By the use of the three dimensional features problems of edge effects such as diffraction for laser beams for reading and writing onto the assay areas can be greatly reduced.

In one embodiment the three dimensional features may comprise a plurality of lands in the form of discrete raised areas having substantially planar upper surfaces surrounded by sloping sides and lower non-assay surfaces. This shaping may be termed a mesa formation. The discrete raised areas may have dimensions in accordance with the type and wavelength of laser light being used to read and write the assay areas. The height of the discrete raised areas may be approximately one quarter of the wavelength of the laser beams being used to read and write the discrete raised areas, for instance. Their transverse dimension may be approximately the half power energy diameter of the laser light being used. Their longitudinal dimension may be any convenient length for deposition or synthesis of compounds and subsequent reading such as two to six times the half power energy diameter of the laser light being used. Their longitudinal spacing may be such that a laser beam can be switched on or off between adjacent areas. The transverse spacing may be about half power energy diameter or more of the laser light being used.

In an alternate embodiment the assay surface of the assay disc may be non-planar and include a spiral pattern of raised ridges defined by lands, grooves and side portions between lands and the grooves and the assay surface upon which the features are produced may be on the lands on the spiral ridge or in the grooves between the ridges. By this arrangement good transverse separation of features on the assay surface may be achieved and possible complications with edge effects degrading the quality of features may be avoided. Wavelengths of light and hence the possible spot sizes used to define and read features on the lands or grooves may determine the geometrical features of the lands and grooves and the pitch spacing. In an alternative arrangement the assay surface upon which the combinatorial chemistry features are produced may be on the lands on the spiral ridges and the data surface may be in the grooves between the lands.

The spacing of combinatorial chemistry features on the lands both longitudinally along the lands and between adjacent lands laterally may be such that writing and reading of those features is not interfered with by writing and reading of features on adjacent lands and further along the same land. For instance in the process of fluorescence analysis of DNA fragments it is desirable that the signal intensity of fluorescing samples is not influenced by adjacent features.

In one preferred embodiment the assay surface may be adapted for bio assay of compounds such as DNA fragments. For this purpose the chemically functional layer may be functionalised so that suitable linker molecules for joining of DNA on to the surface can be covalently bonded to the chemically functional layer. The linker molecules may be dendrimers so as to obtain a greater density of oligonucleotides when they are subsequently placed in a selected array on the assay surface.

These dendrimers may be deposited in a selected array using the selective deposition techniques discussed below for the manufacture of DNA arrays. The dendrimer linker molecules may be carried in a charged emulsion as discussed below.

The conductive layer may be a very thin layer and may be transparent. The conductive layer may be vacuum-deposited onto the support. The conductive layer may be selected from a sputtered layer of metal or indium tin oxide, or a carbon nano-tube layer or any other suitable material. The conductive layer may be reflective to provide an amplification effect for light impinging thereon where the layer above the conductive layer is a photoconductor.

The dielectric or photoconductive layer of material which retains an induced electric charge may be an active layer and the charge on this layer may be influenced by radiation selected from infrared, visible, ultraviolet or x-ray.

The dielectric or photoconductive layer may be of a material which is adapted to have a charge pattern formed thereon by selective discharging of an already charged surface upon incident radiation impinging thereon. The already charged surface on the substrate may be provided by a corona discharge, electron beam gun, nanometer electron beam, donor roller or the like.

Alternatively the dielectric layer may be chargeable by processes such as soft lithography. Soft lithography refers to a high resolution charging technique based on transferring a pattern from a conductive elastomeric stamp to a dielectric substance with conformational contact.

The dielectric layer may be glass or a polymeric resin such as methylmethacrylate (MMA) or the like.

Where the dielectric layer is a photoconductor the material of the layer may be selected from zinc oxide, cadmium sulphide, amorphous selenium, alloys of selenium such as selenium-tellurium, lead selenide, selenium-arsenic, and the like. Additionally, there can be selected as photoresponsive imaging members various organic photoconductive materials including, for example, polyvinylcarbazole (PVK) or complexes of polyvinylcarbazole sensitised with trinitrofluorenone. There are also disclosed layered organic photoresponsive devices with aryl amine hole transporting molecules, and photogenerating layers, reference U.S. Pat. No. 4,265,990, the disclosure of which is totally incorporated herein by reference.

Examples of suitable photoconductor materials include ZnO resin dye combinations coated on metallised Mylar™ (PET polyethyleneterephthalate), vacuum evaporated cadmium sulphide, vacuum evaporated selenium, pure selenium, PVK or PVK photoconductor sensitised with trinitrofluorenone (TNF) or other dye.

Polyvinylcarbazole (PVK) may also be used without the addition of a sensitiser. This has the advantage that the charged photoconductor can be discharged using an optimum wavelength of 345 nm. The pure PVK photoconductor can be exposed by a modified Blu Ray™ optical recording system by substituting the standard 405 nm Blu Ray™ diode with a 345 nm diode for writing purposes. Pure PVK is transparent.

Alternatively the use of polyvinylcarbazole which has been sensitised using dyes to be photoconductive in the region of 405 nm wavelength but which do not emit luminescence or fluorescence at this wavelength may be advantageous. This would allow tags or fluorescent markers which are attached to the hybridised labelled DNA on the array surface to be read using a laser with light with a wavelength in the region of 405 nm, that is, the same wavelength as that used for writing the array.

Hence commercially available lasers with a wavelength in the region of 405 nm may be used for both writing and reading.

Polyvinylcarbazole may be deposited by vapour deposition or by spin coating of a solution of PVK. Laser ablation may be used to selectively remove the PVK in selected regions if necessary.

The chemically functional layer acts as a barrier layer to prevent access or reaction between the liquids or reagents in the emulsion and other liquids used in the synthesis process and components of the dielectric or photoconductive layer. Alternatively or in addition the chemically functional layer may be a reactive material which allows a chemical reaction with another compound at its surface to form a derivatised or functionalised surface for subsequent reaction such as with linker molecules. Alternatively the chemically functional layer may be intrinsically reactive and provide a binder molecule or linker molecule function. The chemically functional layer is an electrical insulator.

The chemically functional layer may be formed from a silane, silicon dioxide, silicon nitride ($Si_xN_y$), titanium dioxide, Tyzor™, cross-linked or partially cross-linked epoxy novolac resin, polymerised oligomers, cross-linked resins, functionalised parylene (a polymer of di-para-xylyene with one or more functional groups), acrylates and methacrylates which may include functional groups, multi-acrylate and methacrylate monomers, monomers which have been cross-linked with a photo-initiator and the like. Multi-acrylate and methacrylate monomers refers to monomers with a plurality of double bonds. The functional group may be an active ester, epoxy, aromatic, acid, aliphatic and hydroxyl or the like.

Formation of the chemically functional layer may be achieved using several processes, including immersion of the substrate in reactive chemicals, painting, dip-coating, spin-coating, vacuum deposition and vapour phase deposition, wherein the chemically functional layer becomes attached by covalent bonding or by other attractive forces after solvent evaporation or curing of resins by heating, irradiation e.g., with UV light, by treatment with peroxides or catalysts or by free radical mechanisms. Such layers may be formed either in air or under an inert atmosphere such as nitrogen.

There may be provided on the chemically functional layer by various deposition techniques a pattern of a non-wetting material so as to inhibit deposition of biochemical arrays in unwanted regions on the assay disc. For instance in the case of an assay disc comprised of lands and grooves with the biochemical features on the lands and the address data pattern on the grooves then the sides of the surface between the lands and the grooves and the grooves themselves may be coated with a non-wetting composition such as a fluorine or silicone based composition.

The conductor layer, where the data layer is to be read through the assay surface, may be a transparent conductor such as indium tin oxide (ITO) or a thin gold or silver layer for instance. Where the assay surface is on the surface opposite to the one through which the data layer is read then the conductive layer may be opaque.

The formation of the assay surface in the photo-conductor activated form of the invention is further disclosed in co-pending PCT application No. PCT/AU2004/000865 the disclosure of which is incorporated herein in its entirety by reference.

As discussed above the data surface preferably comprises a spiral of readable spots such as pits or regions of a different colour or texture formed into a reflective surface. The features, such as biochemical assay features on the surface of the assay disc of the present invention, may be of a similar size to the pit features on the data surface or may be sized at any convenient size. The minimum area of a biochemical assay feature for instance may depend upon the practical limits for reading of a disc, the width of such a feature may allow for the amount of jitter and/or radial movement in a spinning disc on a disc carrier or turntable and the minimum size that a laser beam of a selected wavelength can be conveniently focused down to. A feature may be substantially square or rectangular or may be oblong or sausage shaped in a similar line to the spiral of pits or the like on the data surface.

The features, such as biochemical assay features on the surface of the assay disc of the present invention, may have dimensions in accordance with the type and wavelength of laser light intended to be used to read and write the assay areas. Their transverse dimension may be approximately to the half power energy diameter of the laser light being used. Their longitudinal dimension may be any convenient length such as two to six times the half power energy diameter of the laser light being used. Their longitudinal spacing may be such that a laser beam can be switched on or off between adjacent areas. The transverse spacing may be about half power energy diameter of the laser light being used.

Hence, for an optical disc based upon CD technology the width of an assay feature may be 0.5 to 2 microns and the length may be from 1 to 10 microns with a track pitch of from 1 to 5 microns. Spacing circumferentially between features may be from 1 to 5 microns. For an optical disc based upon DVD technology the width of a feature may be 0.3 to 1 micron and the length may be from 0.3 to 5 microns with a track pitch of from 1 to 2 microns. Spacing circumferentially between features may be from 0.5 to 3 micron. For an optical disc based upon Blu Ray™ technology the width of a feature may be 0.2 to 0.5 microns and the length may be from 0.2 to 1 micron with a track pitch of from 0.5 to 2 microns. Spacing circumferentially between features may be from 0.2 to 1.5 micron.

Lasers for writing and reading an optical disc based upon CD technology may have a spot size of about 2.1 microns first ring diameter, a half energy diameter of 1.6 microns and an effective energy diameter of 1 to 1.5 microns diameter depending upon the type of photoconductor being used and the amount of light needed to sufficiently discharge the photoconductor. Lasers for writing and reading an optical disc based upon DVD technology may have a spot size of about 1.3 microns first ring diameter, a half energy diameter of 1.1 microns and an effective energy diameter of 0.5 to 1 microns diameter depending upon the type of photoconductor being used and the amount of light needed to sufficiently discharge the photoconductor. Lasers for writing and reading an optical disc based upon Blu Ray™ technology may have a first ring size of about 0.6 microns diameter, a half energy diameter of 0.5 microns and an effective energy diameter of 0.2 to 0.4 microns diameter depending upon the type of photoconductor being used and the amount of light needed to sufficiently discharge the photoconductor.

In general the manufacture of DNA arrays onto the substrate involves the selective and sequential addition onto the substrate, of molecular units each with a protective group which is removed when the next molecular unit is to be added. One such method of manufacturing DNA arrays uses a process known as the phosphoramidite process which uses a trityl group or derivatives of the trityl group as the protective group. The invention is not limited to this process but will be discussed with respect to it.

The phosphoramidite process is a repetitive four stage process (deprotection, coupling, capping and oxidation) for the chemical synthesis of polymers particularly sequences of DNA oligonucleotides to form portions of DNA.

In the phosphoramidite process, a portion of DNA in single stranded form is built up by the sequential addition in predetermined order of any one of the four nucleotides (in phosphoramidite form) being the four components which make up DNA, the A, T, G and C nucleotides. Each nucleotide has a chemically removable protecting group on it. A chemical reagent known as a de-protecting agent or detrytilation agent removes the protecting group exposing a reactive hydroxyl group and in the next stage a nucleotide (in phosphoramidite form) is coupled to the growing DNA string. The next stage is a capping step where any DNA strings which were de-protected but to which a nucleotide was not coupled are permanently capped to prevent unwanted addition of nucleotides from adding to that molecule in later coupling steps. In the fourth and final step, oxidation of the newly formed internucleotide phosphite linkage is carried out to convert the linkage to a phosphotriester.

In the manufacture of DNA arrays, a number of different sequence DNA strands are built up on a substrate to enable later biochemical analysis to take place. In this process it is necessary to selectively de-protect various portions of the array and it is particularly to substrates which allow this selective de-protecting that the present invention is directed.

The method of forming a DNA array on the assay surface can use a stepwise coupling process with a chemical de-protecting step prior to each coupling step, the method including the steps of:

(a) defining at least one region on the assay surface by forming an electric or electrostatic charge on that region which is different from the electric or electrostatic charge on other regions of the assay surface such as by formation of an electrostatic image thereon,
(b) applying an emulsion to the assay surface, the emulsion having an electrically charged discontinuous phase and a chemical de-protecting reagent carried in the discontinuous phase,
(c) attracting the discontinuous phase of the emulsion to the at least one preselected region by attraction by the electric field on the region and optionally by the use of a bias voltage,
(d) causing chemical de-protecting in the at least one region,
(e) removing the emulsion, and
(f) carrying out subsequent steps of the stepwise coupling process.

The subsequent steps of the stepwise coupling process may be such as those that are carried out in the standard phosphoramidite chemistry for synthesis of oligodeoxynucleotides although as discussed earlier the invention is not limited to this particular chemistry.

It will be realised that the process as discussed above may be repeated a sufficient number of times to synthesize selected oligonucleotides of any sequence in a predetermined spatial order, position and length on the assay surface.

It will be realised that by the use of an assay disc as the substrate upon which the formation of features takes place then the features will be formed into a spiral on the assay surface in a similar form to the spiral of data pits on the data surface. Hence any feature can be conveniently addressed in relation to its position with respect to the data pits on the data surface. Hence at least some of the data pits on the data spiral can provide address information for a corresponding assay feature.

The step of defining at least one region on the assay surface by forming an electric or electrostatic charge on that region may include the assistance of a bias voltage to control attraction and deposition of the electrically charged discontinuous phase of the emulsion in the selected region.

Deposition may be done with the assistance of a bias voltage. A bias voltage may be supplied by the use of a bias plate which is placed a selected distance above the substrate and a voltage (1 to 100V) applied to the bias plate with respect to the conductor layer. The voltage of the bias voltage needed can depend upon the distance of the substrate from the bias plate, the original level of electrostatic charge and the residual level of electrostatic charge. The voltage applied to the bias plate can be negative or positive. Bias voltage is used to prevent deposition in unwanted regions, to control the density of deposition and/or to cause reversal deposition.

Where the emulsion droplets are positively charged the use of a positive voltage on the bias plate may assist with reduction of deposition at unwanted regions of the substrate surface. Where the emulsion droplets are negatively charged the use of a negative voltage on the bias plate will assist with deposition at non-negatively charged regions of the substrate surface.

The formation of the electric or electrostatic charge may be by electrostatic means such as wherein the assay surface includes a photoconductor and the formation of the electrostatic field is by electrostatic or other charging and then selective discharge by illumination. Preferably the illumination may not include radiation in the short ultraviolet region as this may cause damage to the DNA molecule. For the assembly of other chemical assay discs or arrays, however, UV radiation may be used.

The step of removing the emulsion may include the step of neutralising any residual chemical de-protecting agent in the emulsion to prevent it from reacting in non-desired parts of the array. The step of removing the residual fluids may be done by spinning the disc.

The emulsion for use for the present invention may comprise an electrically insulative continuous phase such as a fluorochemical, an aqueous or a non-aqueous discontinuous phase for instance a hydrocarbon oil which carries the reactive agent or chemical de-protecting agent in it in solution, with preferably a surfactant and preferably a charge control agent.

Where the discontinuous phase is water the chemical de-protecting agent may be a weak organic acid such as acetic acid. Acetic acid may be present in a concentration of up to 80% by volume.

Where the discontinuous phase is a hydrocarbon oil, the chemical de-protecting agent may be a strong protic organic or inorganic acid.

The non-aqueous discontinuous phase which carries the chemical de-protecting agent in solution may be selected from acetone, acetonitrile, cyclohexanone, dibromomethane, dichloromethane (methylene chloride, DCM), trichloromethane, dimethyl formamide (DMF), dioxane, 1,2-dichloroethane (DCE), nitromethane, tetrahydrofuran, toluene, dimethyl formamide or mixtures of compounds such as isopropanol/methylene chloride, nitromethane/methanol, nitromethane/isopropanol, trichloromethane/methanol or isopropanol/methylene chloride. Other hydrocarbons such as decalin may also be used.

The chemical de-protecting agent may be a Lewis acid or a protonic acid. The Lewis acid may be selected from but not restricted to zinc bromide, titanium tetrachloride, and ceric ammonium nitrate while dilute protonic acids which can be used include, but are not limited to, dilute mineral acids, trichloroacetic acid (TCA), dichloroacetic acid (DCA), benzenesulphonic acid, trifluoroacetic acid (TFA), difluoroacetic acid, perchloric acid, orthophosphoric acid and toluenesulphonic acid. Other acids may include dodecylbenzene sulphonic acid and diphenyl acid phosphate.

The manufacture and use of emulsions for the present invention is further disclosed in co-pending PCT application No. PCT/AU2004/000863 the disclosure of which is incorporated herein in its entirety by reference.

Although the invention has generally been discussed in relation to its application to DNA analysis it will be realised that other forms of assay and combinatorial chemistry, for instance, deposition of proteins, may be carried out using the device of the present invention.

The manufacture of spatial arrays by the use of combinatorial chemistry on the assay surface in the photo-conductor activated form of the invention is further disclosed in co-pending PCT Application No. PCT/AU2004/000864, the disclosure of which is incorporated herein in its entirety by reference.

The process of use of the assay disc according to the present invention, in its use as a DNA analysis device for instance, requires that in a first step an array of DNA oligomers are deposited onto the assay surface in a known array. A disc prepared for diagnosis of a particular disease or condition for instance, can be prepared in advance and supplied or sold to a user. Alternatively an assay disc can be prepared at the time it is to be used. The latter may be useful in research situations.

To carry out analysis on a sample which possibly contains DNA of interest the sample in a suitable suspension is prepared with a tag or fluorescent compound attached to each of the DNA fragments. The sample is passed over the array surface and DNA hybridisation occurs where matching DNA is located on the disc surface. These sites can be located by location of the fluorescing or tag compound.

The fluorescing or tag compound may be a dye but problems with dyes include fading so that a subsequent pass of a detector over the assay surface may not elicit a fluorescent response.

Alternatively the target DNA (from the patient or source) may be tagged with Quantum Dots (QDot™) or equivalent, tuned to emit light when exposed to a standard 405 nm Blu Ray™ laser used in the latest state of the art optical recording systems. QDOts™ tuned to 405 nm wavelength are standard materials. The light emitted from the QDot™ tagged DNA would be collected and measured by a photo diode to identify the target DNA (patient's).

The use of a Quantum Dot with an adsorption wavelength of 405 nm to tag the DNA has three major advantages.

(1) The Quantum Dot tagged DNA puts out ×1000 the amount of light compared to the normal long wavelength organic dyes currently used for tagging the target DNA.
(2) Quantum dots do not fade with exposure to light as do the current normal organic dyes used for tagging such as dye conjugate Cy3 Streptaviadin.
(3) Mass produced Blu Ray™ disc reader hardware is readily available and with minimum modification can be converted to read the hybridised 405 nm QDot™ tagged DNA.

This then generally describes the invention but to assist with understanding reference will now be made to the accompanying drawings which show preferred embodiments of the invention.

DESCRIPTION OF PREFERRED EMBODIMENTS

Figure 1:
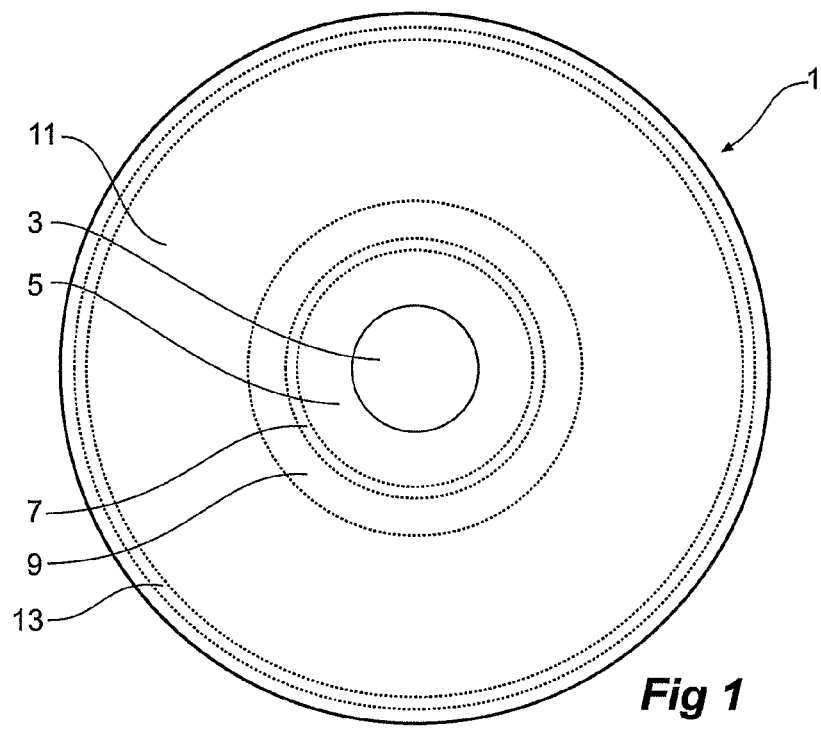
FIG. 1 shows a general view of a disc such as a optical disc suitable for the present invention.

Now looking more closely to drawings and in particular in FIG. 1 it will be seen that an assay disc according to one embodiment of this invention is a substantially planar circular disc 1 with a central aperture 3 for mounting onto a turntable to enable it to be rotated. An area 5 around the aperture 3 is used to clamp the disc onto the turntable for accurate turning. An area 7 on the disc outside the clamp area 5 is a run in area which enables a laser tracking device on the disc to locate the commencement of the data spiral on the disc and if desired to provide some address information for the disc. Outside the area 7 is a program area 9 in which data relating to the type of assay disc, software for managing the disc, any analysis information and address information for features on the disc can be provided.

The majority of the area 11 of the disc is a combined data area and assay area with the data area being within the disc and the assay area being on an outer surface of the disc as will be discussed later. Finally there is a run out area 13 which defines the outer tracking area and the termination of the data spiral and assay spiral.

It will be realised that the regions 3, 5, 7 and 13 and the data area of 9 are known from existing optical disc reading and writing technology. Area 11 would, in existing optical disc reading and writing technology, be included with the data area 9.

Figure 2:
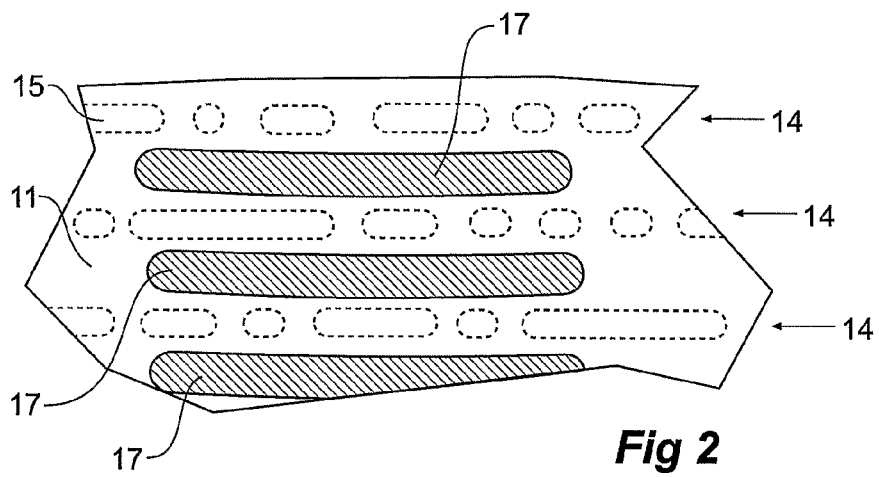
FIG. 2 shows in schematic detail a portion of an assay disc according to one embodiment of the present invention.

FIG. 2 shows a plan view of a portion of the disc of FIG. 1. Essentially in the regions 7,9, 11 and 13 of FIG. 1 there is a spiral 14 of data pits, one of which is shown as 15 in FIG. 2 and which are set within the disc as will be discussed below. On the surface of the disc according to the present invention there may be a plurality of features 17 placed again in a spiral form. These features comprise, for instance, predetermined groups of oligomers formed by the method discussed above and which can be used to analyse the DNA in a sample. In practice a number of different oligomers are formed into separate features on the disc and where a DNA fragment sample hybridises to a specific oligomer then the type of DNA in the sample can be determined.

Figure 3:
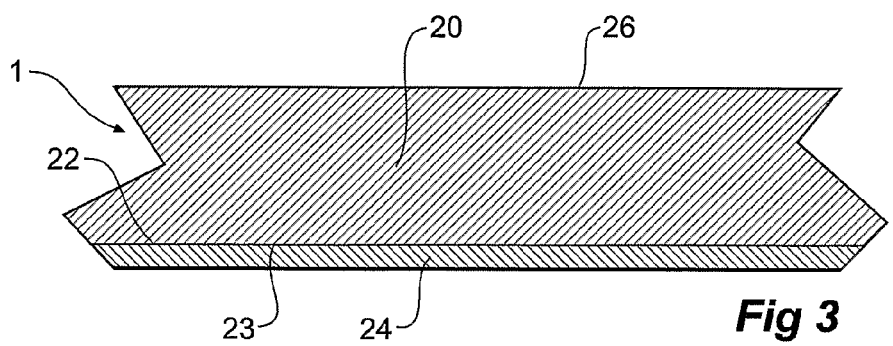
FIG. 3 shows a detailed cross section of one embodiment of a disc according to the invention.

FIG. 3 shows cross section of a portion of the assay disc of FIG. 1. The assay disc 1 comprises a base 20 of a transparent material such as polycarbonate and within the base 20 is a data surface 22. Underneath the data surface is a physical protection layer 24 for protecting the data surface from scratches or the like. On the surface of the base 20 is an assay surface such as a bio assay surface 26. The nature of the data surface 22 and assay surface 26 will be discussed in detail below. Between the data surface 22 and the physical protection layer 24 is a reflective layer 23.

Figure 4:
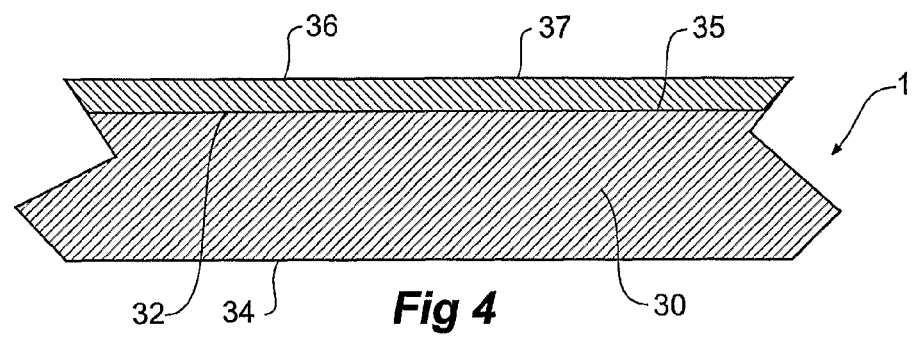
FIG. 4 shows a cross section of another embodiment.

An alternative arrangement of assay disc according to this invention is shown in cross section in FIG. 4. In this embodiment the disc 1 has a base 30 formed from a transparent plastics material such as polycarbonate and a data surface 32 which can be read through the base from the lower surface 34. The upper surface 36 of the disc comprises an assay surface with a physical protection layer 37 between the assay surface and the data surface 32. Once again the construction of the various layers will be discussed below. Between the data surface 32 and the physical protection layer 34 is a reflective layer 35.

Figure 5:
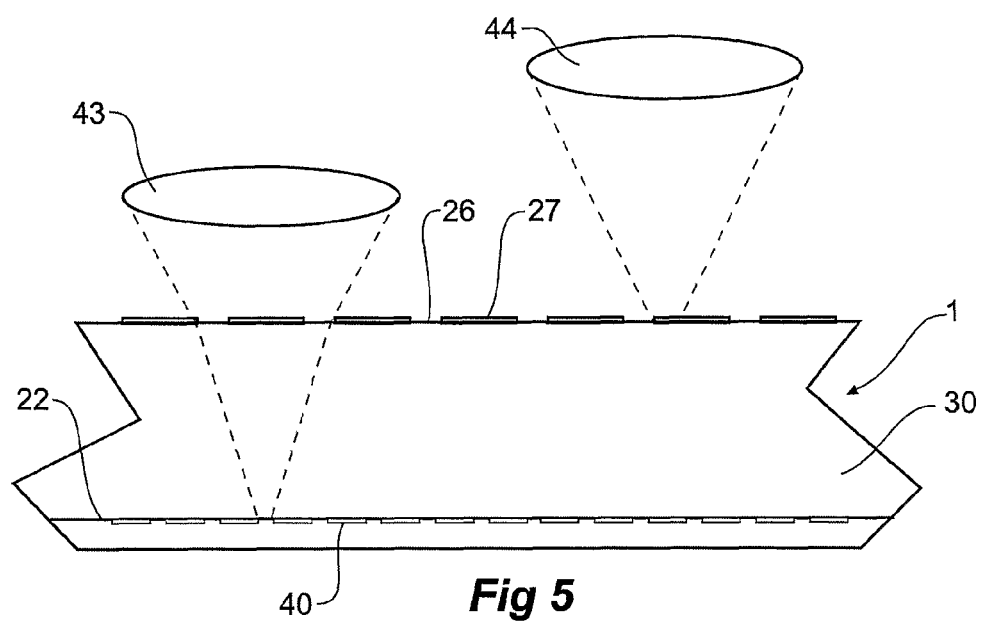
FIG. 5 shows how, using the embodiment of FIG. 3, information may be read from both the data surface and assay surface.

FIG. 5 shows a detail of the disc 1 according to the embodiment shown in FIG. 3 and shows how the lasers can read each of the surfaces. The data surface 22 comprises a number of pits 40 and these are read by means of a laser 42 which is relatively unfocused at the assay surface 26 and is hence relatively unaffected by features 27 on the assay surface 26 but is focused at the pits 40 so that the existence or not of a pit in the spiral lines of pits of the type shown as 14 in FIG. 2 can be determined.

The assay surface 26 can be written to by the electrophotographic methods discussed above by means of a laser 44. This laser 44 is focused at the assay surface 26 to form and read the features 27 and hence is not affected by the data surface 22 within the base 30. Similarly when the assay surface is to be read by the laser 44 then this laser is focused at the assay surface 26 and is not affected by the data surface 22 within the base 30.

Figure 6:
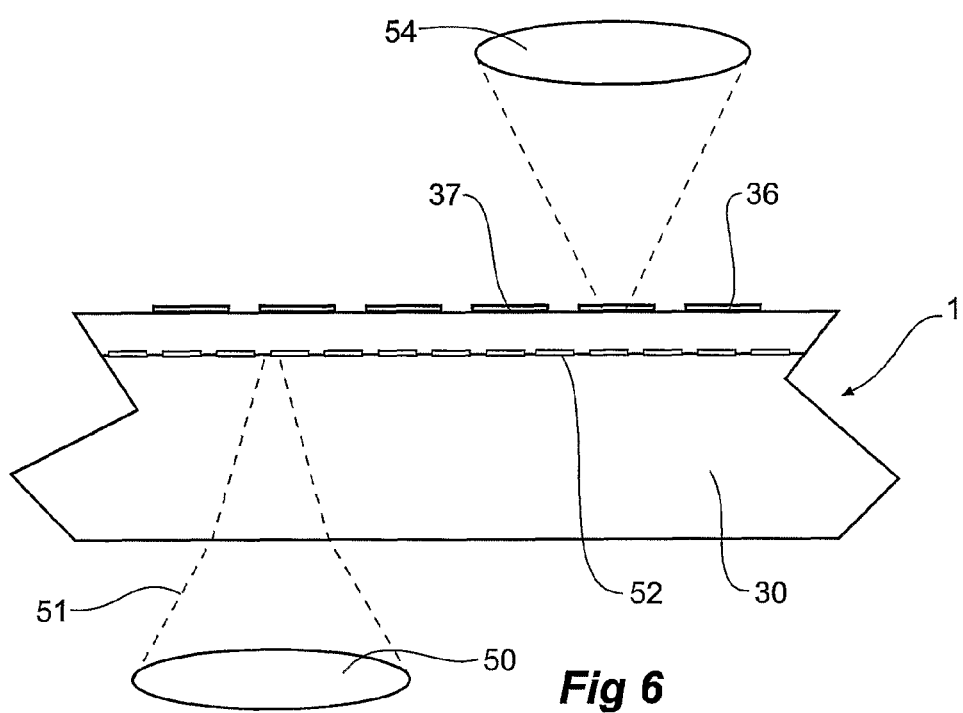
FIG. 6 shows how, using the arrangement of FIG. 4, information may be read from both the data surface and assay surface.

In the embodiment shown in FIG. 6 a disc 1 according to the embodiment shown in FIG. 4 shows laser 50 focused on the data surface 52 through the base 30 and the assay surface 36 is written to and read by the laser 54 which is focused on the assay surface 36 and interference between the two lasers does not occur.

Figure 7:
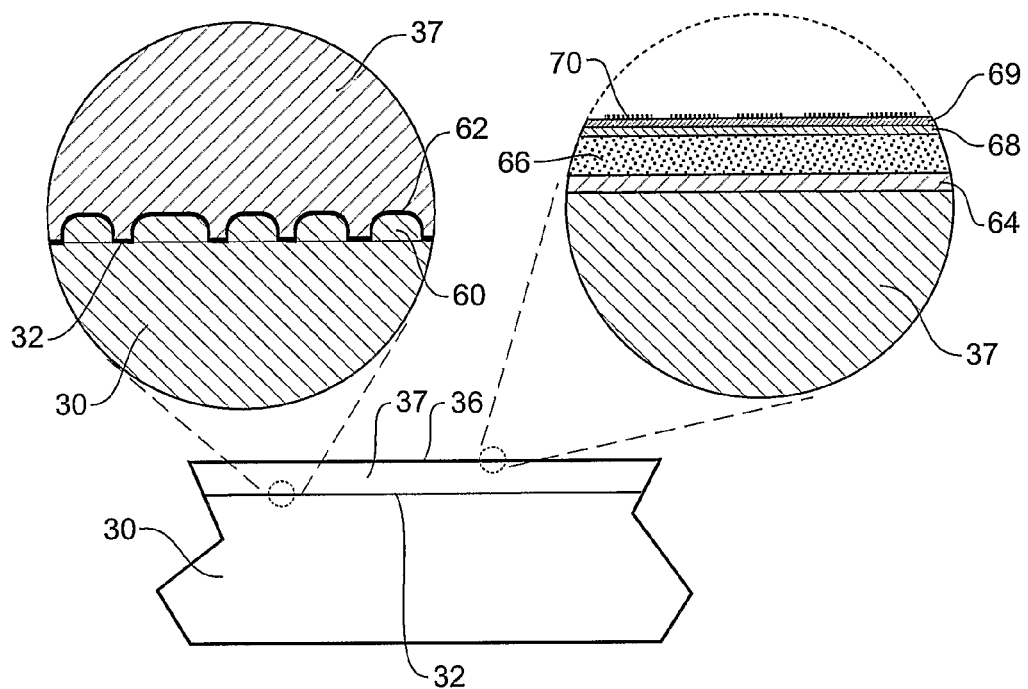
FIG. 7 shows in detail the structure at the data and assay surfaces for the embodiment shown in FIG. 4.

FIG. 7 shows details of the data and assay surfaces of the embodiment shown in FIGS. 4 and 6. The data surface 32 comprises a plurality of pits 60 with a reflective surface 62 behind them. The laser 50 as seen in FIG. 6 reads the pits through the base material 30.

The assay surface 36 is formed on the protective layer 37 and consists of a thin conductive layer 64 formed onto the protective layer 37 and then a photo-conductor 66 formed onto the conductor 64. On the photo-conductor 66 is a protective layer 68 and on the protective layer 68 is a chemically functional layer 69. It is on the chemically functional layer that a defined DNA oligonucleotide 70 can be formed.

Figure 8:
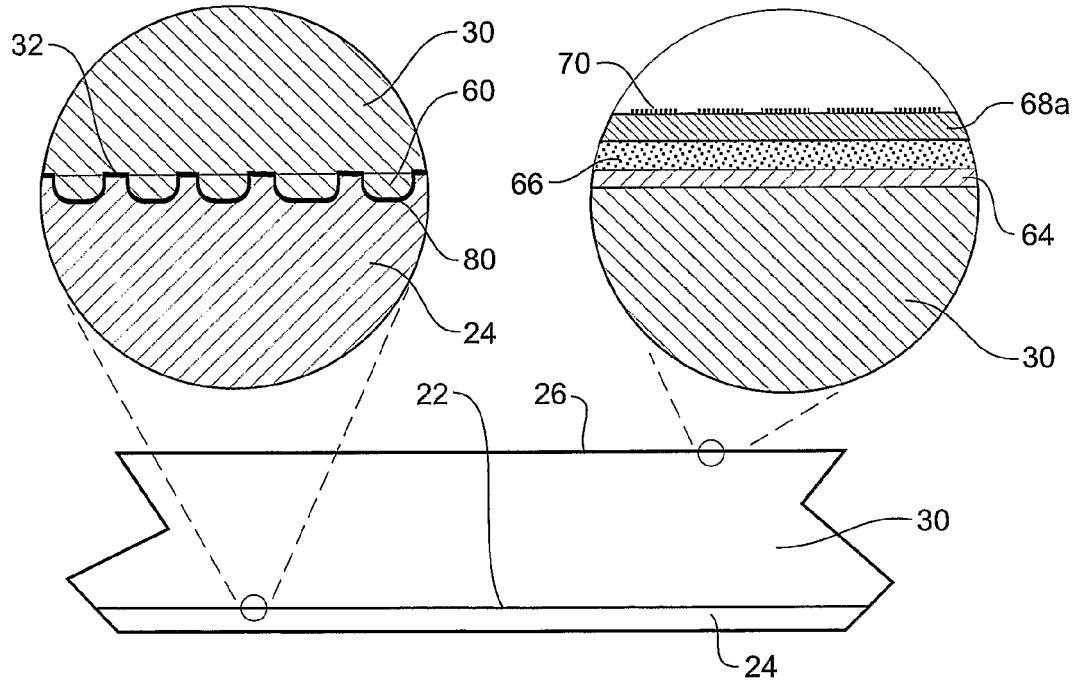
FIG. 8 shows detail of the structure at the data surface and assay surface of the embodiment shown in FIG. 3.

FIG. 8 shows the detailed construction of the data surface and assay surface of the embodiment shown in FIGS. 3 and 5. In this arrangement the data surface 22 is formed as a reflective layer 80 between the protective layer 24 and base 30. The reflective layer 80 has a number of pits 60 formed into it which are read by the laser 42 (see FIG. 5) to enable data to be obtained.

The assay surface is similar in construction to that of FIG. 7 except that it is formed on the upper surface of the base 30. The data surface consists of a conductor layer 64, a photo-conductor layer 66 and a chemically functional layer 68a and upon which is formed a defined DNA oligonucleotide 70. In this embodiment, however, as the data surface is read through the assay surface the conductor 64 is transparent or substantially transparent to the wavelength of laser used for the reading of the data surface. The conductor 64 may be formed from indium tin oxide or from a very fine gold or silver coating, for instance, which at a thickness which is necessary for the conductivity characteristic can be transparent. In this embodiment the functions of the protective layer and the chemically functional layer are combined in a single layer 68a.

Figure 9:
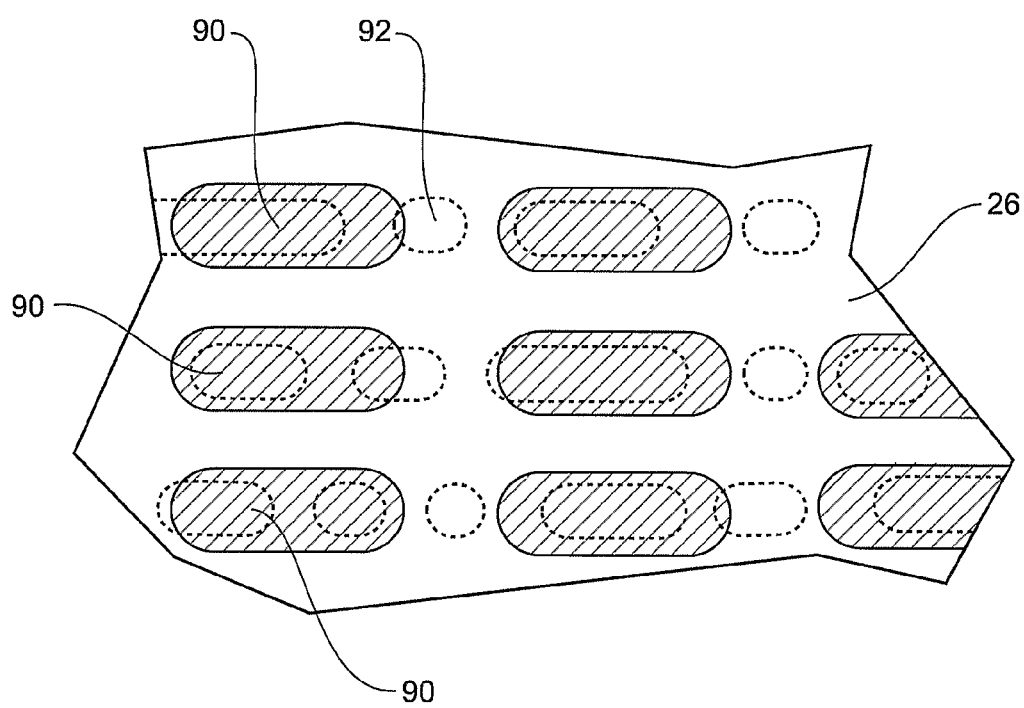
FIG. 9 shows an alternative arrangement of features in detail on an assay disc according to one embodiment of the invention.

FIG. 9 shows an alternative arrangement of features on a portion of the surface of an assay disc according to the present invention. In this embodiment the features 90 on the assay surface are about twice as wide as the spiral of pits 92 on the data surface. The features are spaced apart transversely by a distance which allows for any jitter caused by tracking of the laser onto the assay disc as well as so that laser energy from one track does not detrimentally influence the electrostatic charge on adjacent assay features. Longitudinal spacing of the assay features is sufficient to enable a laser to be switched on or off between the assay features.

If will be realised that the actual placement of the assay features 90 on the surface 26 does not have to be aligned with the spiral of data pits 92 on the data surface but provided a spatial relationship between the two is known then the features can be at any selected place on the disc.

Figure 10A:
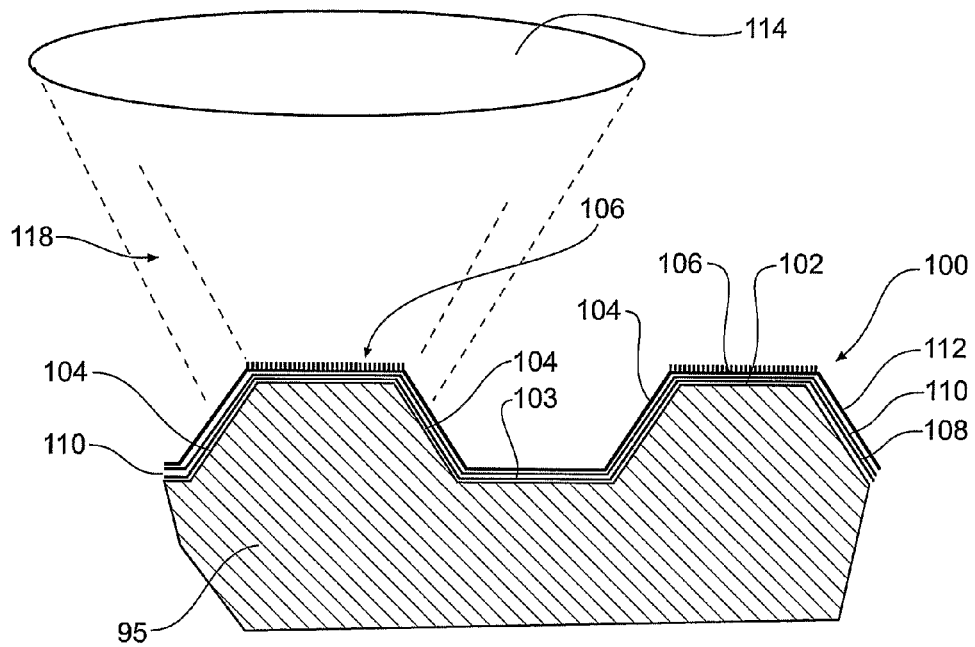
FIGS. 10A and B shows alternative arrangements of assay surfaces including a spiral ridge in a particular embodiments of disc substrates for combinatorial chemistry according to the present invention.

FIGS. 10A and B shows alternative three dimensional arrangements of assay surfaces including a spiral ridge in particular embodiments of disc substrates for combinatorial chemistry according to the present invention In this embodiment there is a spiral embankment or ridge and a spiral groove between the ridge on the assay surface and the material to be assayed and the material such as DNA oligonucleotides to be used for the assay can be formed on the ridge or in the groove of the spiral surface.

Figure 10B:
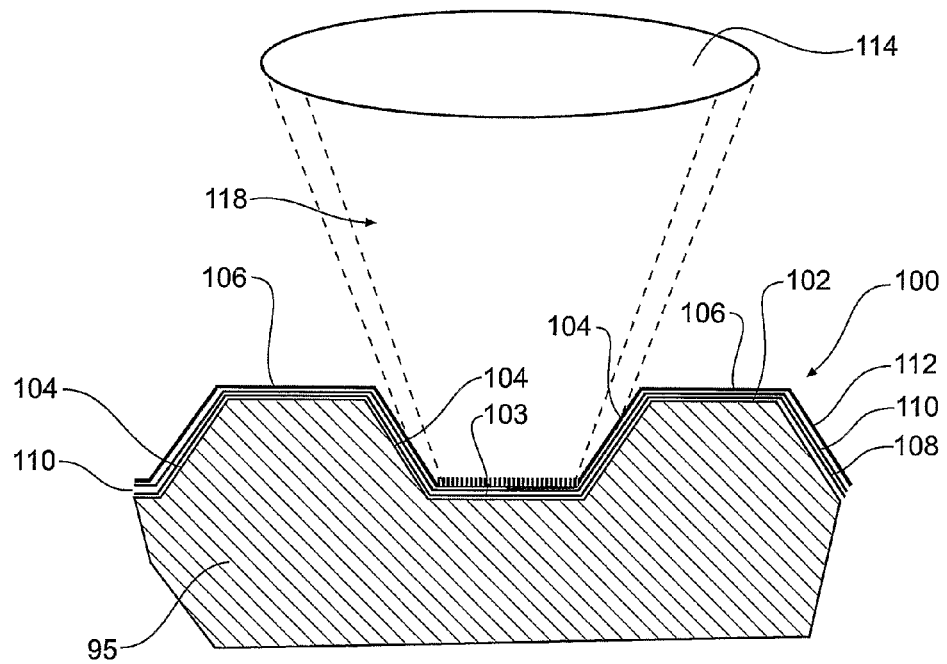

In each of the embodiments shown in FIGS. 10A and 10B the spiral surface consists essentially of the base 95 with a spiral ridge and groove arrangement moulded into the base 95 by suitable moulding techniques. The ridge 100 comprises an upper land 102, sides 104 between the lands and grooves 103 between the sides 104. The assay surface comprises conductor layer 108 photo-conductor layer 110 and chemically functional layer 112 are formed over the entire surface of the disc.

In FIG. 10A the assay elements such as oligomers 106 are formed on the lands 102. When the laser 114 is used to write and read the assay surface only that portion of the laser beam 118 which impinges upon the land 102 is utilised and the portions of the laser beam which impinges on the side regions 104 are lost.

In FIG. 10B the assay elements such as oligomers 106 are formed in the grooves 103. When the laser 115 is used to write and read the assay surface only that portion of the laser beam 118 which impinges upon the land 102 is utilised and the portions of the laser beam which impinges on the side regions 104 are lost.

Using only a central region of the laser beam can give better accuracy for writing and reading of the surface and negate edge effects such as may be caused by inaccurate placement of the various features.

In a preferred arrangement the height of the ridges may be approximately one quarter of the wavelength of the laser beams being used to read and write the lands for instance. The angle of the sides between the land and grooves may be selected so as to maximise the charge remaining on the side surfaces when a laser light is used to selectively discharge regions of the lands. Some of the laser light may spill onto the side surfaces and the angle of the side surface will mean that the light is spread over a larger surface area thereby minimising discharge.

Figure 11:
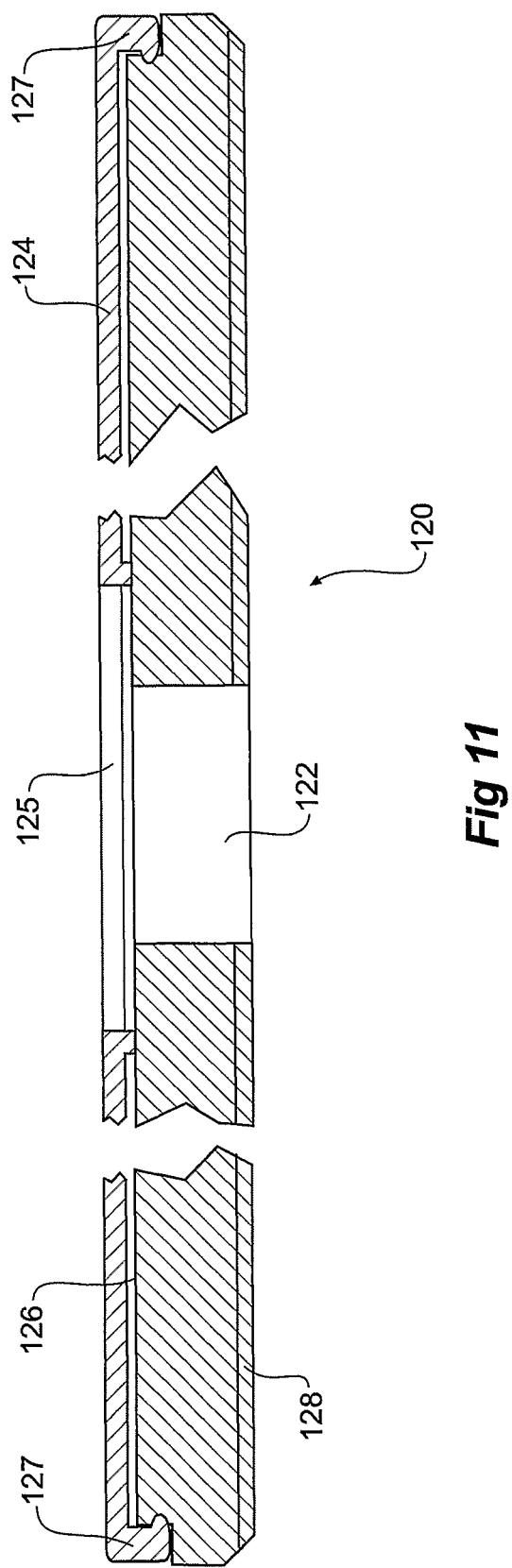
FIG. 11 shows an assay disc including a cover according to the present invention.

FIG. 11 shows a cross section of a disc of the type shown in FIG. 1 with a removable cover on it. The disc generally shown as 120 has a central aperture 122 to enable to be mounted onto a disc turntable but the disc includes a removable cap 124 which clips onto the edges of the disc and provides protection for the assay surface 126 on the disc. Protection may be from dust or water or other chemicals or reagents.

In some embodiments the data surface 128 can be read through the transparent lid 124 because once again the laser is relatively unfocused where it would pass through the lid but in other embodiments the lid may be removed either mechanically or manually to enable reading of the assay surface 126 as well as the data surface 128.

It will be realised that in other embodiments the lid may be a permanent feature on the assay surface and suitable apertures and dividers to delineate portions of the assay surface may be provided for addition of reagents and assay samples. In this way the assay disc may be used for multiple assays.

Alternatively the disc may be supplied in a dust proof cassette from which the disc can be removed automatically within a dust free environment of a writing, hybridisation or reading device.

Figure 12:
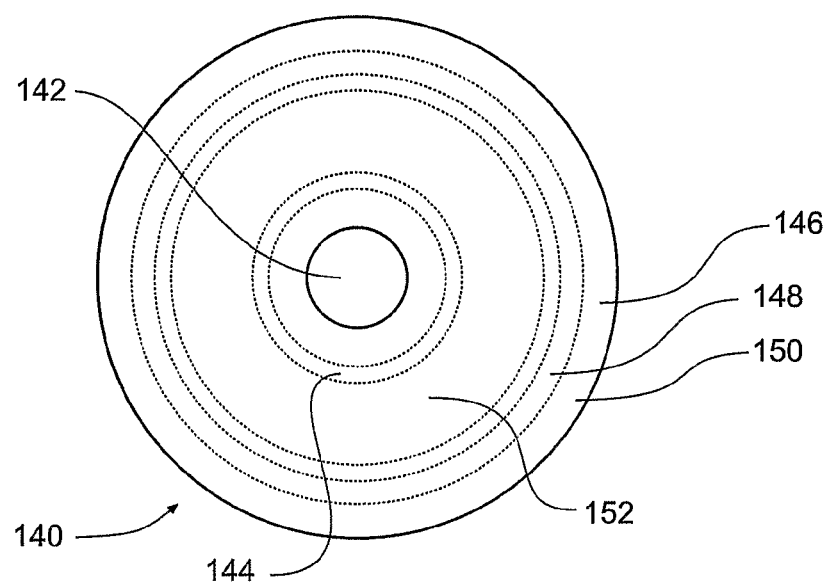
FIG. 12 shows a plan view of an assay disc according to an alternative embodiment of the present invention.

FIG. 12 shows a plan view of an assay disc according to an alternative embodiment of the present invention. In this embodiment the assay disc 140 has a central spindle hole 142 and an inner sealing area 144 and an outer sealing area 146. These sealing areas are provided so that the disc can be clamped into a machine to isolate the region between the inner sealing area 144 and the outer sealing area 146 to allow the supply of reagents etc to that region. Inward of the outer sealing area 146 there is a probe area 148 and inboard of that is a lead-in area 150 and the balance of the disc is a blank area 152. The probe area 148 includes the biochemical features for instance and may also include interleaved with it the address data region as discussed earlier.

In one embodiment the disc according to the invention may have a diameter of 58 mm, the inner and outer sealing areas may take up of 2 to 3 mm each of the radius, the probe area may take up 1 to 5 mm of the radius and the lead in area may take up 2 to 5 mm of the radius.

Figure 13:
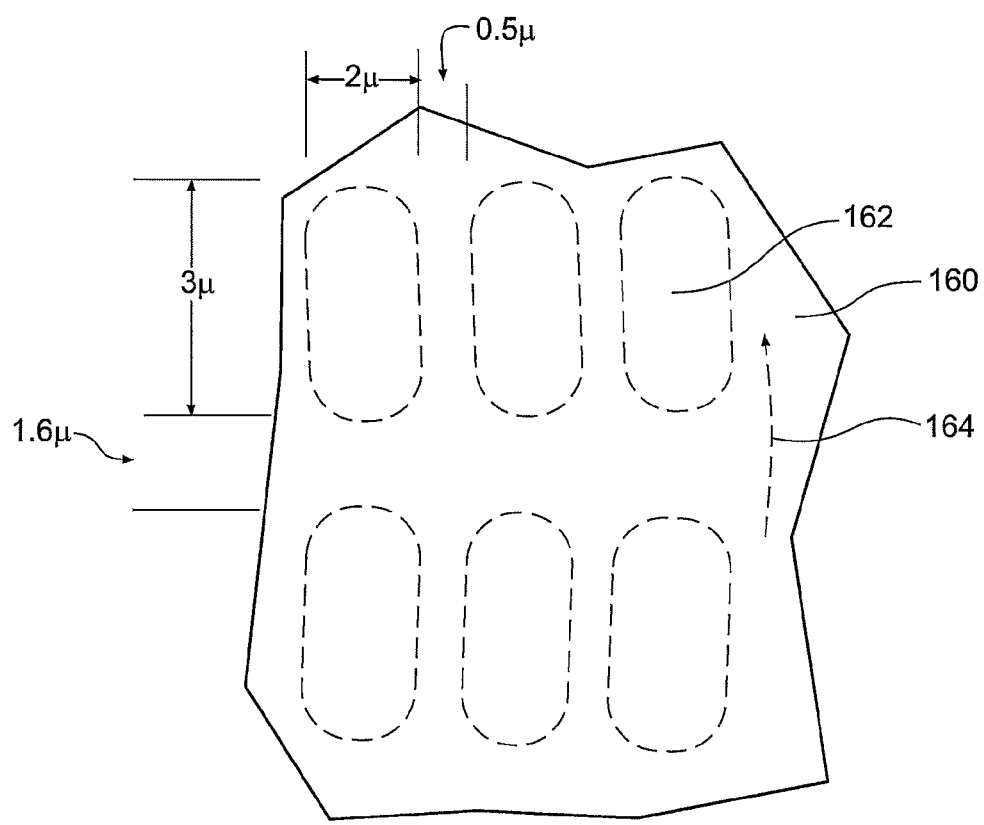
FIG. 13 shows an alternative arrangement of features in detail on an assay disc according to one embodiment of the invention.

FIG. 13 shows an alternative arrangement of features 162 in detail on an assay disc surface 160 according to one embodiment of the invention. In this embodiment the disc is rotated as shown by the arrow 164 and the probe features 162 are of a size of approximately 2μ wide by 3μ long with a longitudinal spacing between probe features of 1.6μ and a transverse spacing between adjacent turns of the spiral of 0.5μ.

FIGS. 14A to E show various stages of application of the present invention in the manufacture of DNA chips using emulsion technology.

Figure 14A:
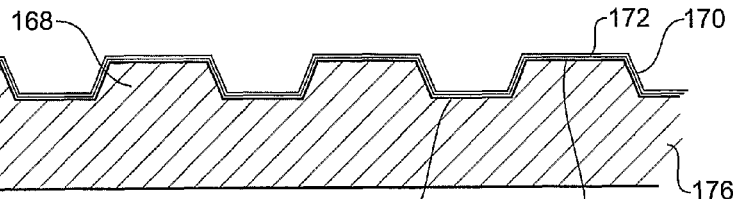
FIGS. 14A to E show various stages of application of the present invention in the manufacture of DNA chips using emulsion technology.

FIG. 14A shows a cross section through optical disc according to another embodiment of the invention.

In this embodiment the three dimensional surface of the assay disc comprises a plurality of raised portions in the form of mesas or lands 168 above the surrounding lower surface 169. The entire surface is covered by layers of the type discussed above. The layers comprise a functional/chemical barrier layer 170, a photoconductor layer 172, a vacuum evaporated metal electrical conductor 174 on a polycarbonate optical disc substrate 176.

Figure 14B:
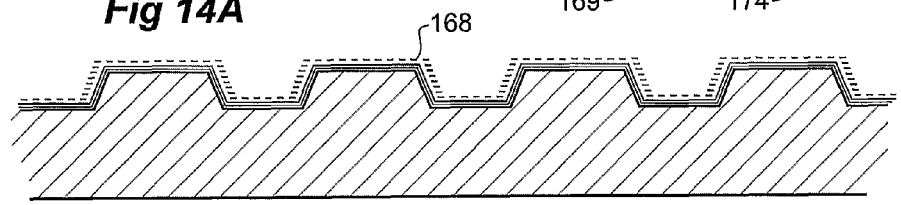

The surface is charged by a corona charging device or other device to give a uniform electrostatic charge 180 as shown in FIG. 14B.

Figure 14C:
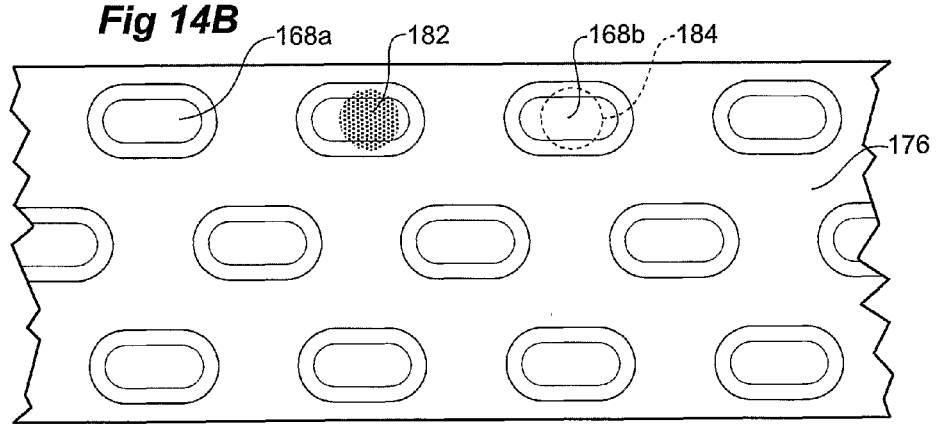

FIG. 14C shows optical disc exposure by laser (in plan view). The shaded circle 184 indicates laser light on which exposes the electrically charged top surface of the three dimensional features 168a on the disc. This causes the photoconductor layer 174 to conduct to the conductor layer 176 which discharges the electrostatic charge in that region. The circle 184 indicates regions where the laser light is switched off and no discharging occurs.

Figure 14D:
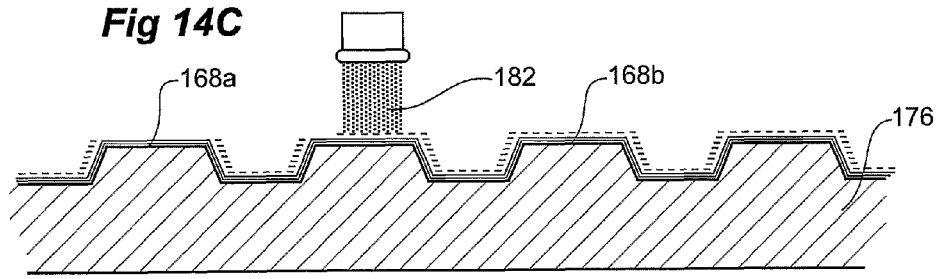

FIG. 14D shows the process in side view. The laser light 182 has discharged the three dimensional features 168a but not the three dimensional features 168b which were not exposed.

Figure 14E:
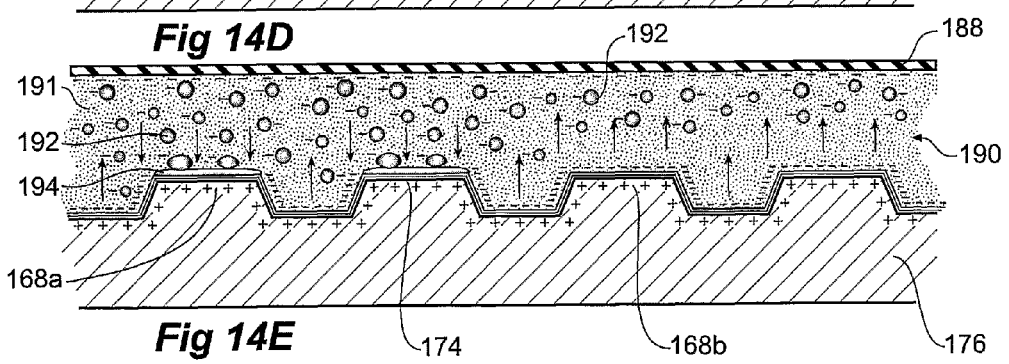

FIG. 14E shows the application of a charged emulsion to the surface of the assay disc. An electrically conductive top plate 188 is clamped onto the disc 176 and forms a sealed chamber 190. A negatively charged potential is applied between the top plate 188 and the electrical conductor 174 which has a positive electrical potential. A negatively charged discontinuous phase emulsion 191 is injected into the chamber.

The negatively charged discontinuous phase 192 of the emulsion 191 is attracted by the positive conductor and deposits and coalesces 194 on the discharged features 168a and is repelled from areas 168b that are negatively charged. The reagent carried on the negatively charged discontinuous phase 192 of the emulsion 191 then carries out the selected chemical reaction such as detritylation at the discharged areas.

Throughout this specification various indications have been given as to the scope of the invention but the invention is not limited to any one of these but may reside in two or more combined together. The examples are given for illustration only and not for limitation.

The invention claimed is:

1. A combinatorial chemical formation and assay disc; the disc comprising a base and an upper surface and a lower surface, one of the upper or lower surfaces comprising an assay surface, a data surface on the upper surface or the lower surface and the data surface being spaced from the assay surface and wherein the data surface is on or within the assay disc, the assay surface comprising a spiral pattern of raised ridges comprising lands, grooves and side portions between the lands and the grooves, the assay surface further comprising a conductive layer on the base, a photo-conductive layer on the conductive layer and a chemically functional layer on the photo-conductive layer, combinatorial chemistry features formed on the chemically functional layer on the lands of the raised ridges or formed on the chemically functional layer on the grooves between the raised ridges, and the side portions between the lands and the grooves providing transverse separation of the combinatorial features on the assay surface wherein the disc comprises a substantially planar disc, a central aperture to receive a spindle and clamping mechanism to enable the disc to be rotated and wherein the conductive layer or an electrical connection from the conductive layer extends to the central aperture of the disc whereby when it is clamped into a processing device the conductive layer is earthed or becomes part of an electrical circuit.

2. The combinatorial chemical formation and assay disc of claim 1 wherein the assay surface and the data surface are spaced radially apart on the disc.

3. The combinatorial chemical formation and assay disc of claim 1 wherein the assay surface comprises a plurality of zones each of which can function as an independent assay surface whereby the disc can be used for a plurality of assays.

4. The combinatorial chemical formation and assay disc of claim 1 wherein the assay surface comprises an array of linker molecules on the chemically functional layer and thereby being adapted for direct photo-conductor activated combinatorial chemistry thereon.

5. The combinatorial chemical formation and assay disc of claim 1 wherein the conductive layer is a conductive material which presents a mirror surface and the photoconductive layer is transparent or translucent whereby the mirror surface provides an increase in light by reflection with a subsequent gain in exposure light efficiency and reading laser light.

6. The combinatorial chemical formation and assay disc of claim 1 wherein the base is transparent whereby data can be read from the data surface through the assay surface and the base.

7. The combinatorial chemical formation and assay disc of claim 1 wherein the assay surface is written or formed and read from one side of the disc and the data surface read from the other side of the disc through the base.

8. The combinatorial chemical formation and assay disc of claim 1 wherein the data surface includes at least a program portion which contains information about how an assay is to be carried out and/or the location of the various features on the assay surface.

9. The combinatorial chemical formation and assay disc of claim 1 further including a lid or cover portion which can be fitted onto the disc on the assay surface side so that the assay surface is thereby protected.

10. The combinatorial chemical formation and assay disc of claim 1 wherein the assay surface upon which the combinatorial chemistry features are produced is on the lands on the spiral ridges and the data surface is in the grooves between the lands.

11. The combinatorial chemical formation and assay disc of claim 1 wherein the assay surface upon which the combinatorial chemistry features are produced is on the grooves and the data surface is on the lands.

12. The combinatorial chemical formation and assay disc of claim 1 wherein the assay surface is adapted for bioassay of compounds such as DNA fragments and the assay surface comprises a chemically functional layer which is functionalized whereby linker molecules for joining of DNA onto the surface can be covalently bonded to the chemically functional layer.

13. The combinatorial chemical formation and assay disc of claim 1 wherein the conductive layer is selected from the group comprising a sputtered layer of metal or indium tin oxide, or a carbon nano-tube layer.

14. The combinatorial chemical formation and assay disc of claim 1 wherein the photoconductive layer is selected from the group comprising zinc oxide, cadmium sulphide, amorphous selenium, alloys of selenium such as selenium-tellurium, lead selenide, selenium-arsenic, organic photoconductive, polyvinylcarbazole (PVK) or complexes of polyvinylcarbazole sensitized with trinitrofluorenone.

15. The combinatorial chemical formation and assay disc of claim 1 wherein the chemically functional layer is selected from the group comprising a silane, silicon dioxide, silicon nitride (SixNy), titanium dioxide, Tyzor™, cross-linked or partially cross-linked epoxy novolac resin, polymerized oligomers, cross-linked resins, functionalized parylene (a polymer of di-para-xylyene with one or more functional groups), acrylates and methacrylates which may include functional groups, multi-acrylate and methacrylate monomers, monomers which have been cross-linked with a photo-initiator.

16. The combinatorial chemical formation and assay disc of claim 6 wherein the conductor layer, where the data layer is to be read through the assay surface, comprises a transparent conductor selected from the group comprising indium tin oxide (ITO), a thin gold layer or silver layer.

17. The combinatorial chemical formation and assay disc of claim 1 wherein the disc comprises a plurality of annular areas including a clamp area adjacent to the aperture, a run in area, a program area defining the data surface, an assay area defining the assay surface and a run out area.

18. The combinatorial chemical formation and assay disc of claim 17 wherein the disc further comprises an inner and an outer circumferential sealing area.

19. The combinatorial chemical formation and assay disc of claim 1 in a sealed cassette to prevent dust reaching the assay surface.

20. A combinatorial chemical formation and assay disc; the disc comprising a base and an upper surface and a lower surface, one of the upper or lower surfaces comprising an assay surface, a data surface on the upper surface or the lower surface and the data surface being spaced from the assay surface and wherein the data surface is on or within the assay disc, the assay surface comprising a spiral pattern of raised ridges comprising lands, grooves and side portions between the lands and the grooves, the assay surface further comprising a conductive layer on the base, a photo-conductive layer on the conductive layer and a chemically functional layer on the photo-conductive layer, combinatorial chemistry features formed on the chemically functional layer on the lands of the raised ridges or formed on the chemically functional layer on the grooves between the raised ridges, and the side portions between the lands and the grooves providing transverse separation of the combinatorial features on the assay surface wherein the disc comprises a substantially planar disc, a central aperture to receive a spindle and clamping mechanism to enable the disc to be rotated and wherein the conductive layer or an electrical connection from the conductive layer extends to the central aperture of the disc whereby when it is clamped into a processing device the conductive layer is earthed or becomes part of an electrical circuit, wherein the assay surface is adapted for bioassay of compounds such as DNA fragments and the assay surface comprises a chemically functional layer which is functionalized whereby linker molecules for joining of DNA onto the surface are covalently bonded to the chemically functional layer.

* * * * *

UNITED STATES PATENT AND TRADEMARK OFFICE
CERTIFICATE OF CORRECTION

PATENT NO.        : 8,551,403 B2  
APPLICATION NO. : 11/908178  
DATED             : October 8, 2013  
INVENTOR(S)       : Peter Hastwell It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 988 days.

Signed and Sealed this

Fifteenth Day of September, 2015

Michelle K. Lee
*Director of the United States Patent and Trademark Office*